(12) United States Patent
Chen et al.

(10) Patent No.: US 7,241,893 B2
(45) Date of Patent: Jul. 10, 2007

(54) THIAZOLINONE 2-SUBSTITUTED QUINOLINES

(75) Inventors: Li Chen, Shanghai (CN); Shaoqing Chen, Bridgewater, NJ (US); Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 101 days.

(21) Appl. No.: 11/224,175

(22) Filed: Sep. 12, 2005

(65) Prior Publication Data
US 2006/0063804 A1 Mar. 23, 2006

Related U.S. Application Data

(60) Provisional application No. 60/610,767, filed on Sep. 17, 2004.

(51) Int. Cl.
*C07D 221/02* (2006.01)

(52) U.S. Cl. .................................................. 546/152
(58) Field of Classification Search ................ 546/152
See application file for complete search history.

(56) References Cited

FOREIGN PATENT DOCUMENTS

| EP | 1 215 208 A2 | 6/2002 |
|----|--------------|--------|
| WO | WO 2004/047760 A2 * | 6/2004 |
| WO | WO 2005/011686 A1 | 2/2005 |

* cited by examiner

*Primary Examiner*—D. Margaret Seaman
*Assistant Examiner*—Nizal S. Chandrakumar
(74) *Attorney, Agent, or Firm*—George W. Johnston; Patricia S. Rocha-Tramaloni; David E. Wildman

(57) ABSTRACT

Thiazolinone substituted quinoline derivatives where the quinoline ring is substituted at the 2 position which derivatives demonstrates CDK1 antiproliferative activity and are useful as anti-cancer agents.

24 Claims, No Drawings

THIAZOLINONE 2-SUBSTITUTED QUINOLINES

PRIORITY TO RELATED APPLICATIONS

This application claims the benefit of Provisional Application Ser. No. 60/610,767, filed Sep. 17, 2004.

FIELD OF THE INVENTION

The field of this invention relates to thiazolinone substituted quinoline derivatives where the quinoline ring is 2-substituted, which derivatives demonstrates CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643–1677 (1996); and *Ann. Rev. Cell Dev. Biol.*, 13:261–291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999).

Because CDKs such as CDK1 serve as general activators of cell division, inhibitors of CDK1 can be used as antiproliferative agents. These inhibitors can be used for developing therapeutic intervention in suppressing deregulated cell cycle progression.

SUMMARY OF THE INVENTION

In accordance with this invention, it has been discovered that the compound of the formula:

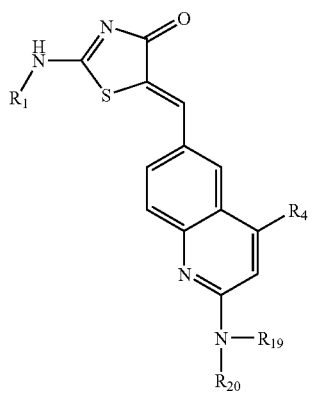

I wherein
$R_1$ is hydrogen, lower alkyl, aryloxy-lower alkyl,

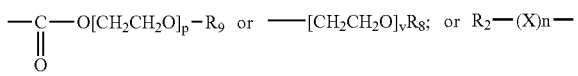

X is lower alkylene, hydroxyloweralkylene, cyclolower-alkylene, aryl lower alkylene, carboxyloweralkylene, hydroxy lower alkylene, amido lower alkylene, mono- or di-halo lower alkylene, amino lower alkylene, mono- or di-lower alkyl amino lower alkylene or imido lower alkylene;

$R_2$ is

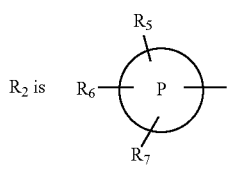

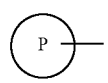

is an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen;

$R_5$, $R_6$ and $R_7$ are independently selected from the group consisting of hydroxy, lower alkyl-sulfone, hydroxylower alkyl, hydrogen, lower alkyl, halogen, perfluro lower alkyl, lower alkoxy, amino, mono- or di-lower alkyl amino, or when two of the substituents $R_5$, $R_6$ and $R_7$ are substituted on adjacent carbon atoms on ring (P), these two substituents can be taken together with their adjacent, attached carbon atoms to form an aryl ring, a 3 to 6 membered cyclolower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

$R_4$ is hydrogen, $-(O)_k(CH_2CH_2O)_y-R_{10}$,

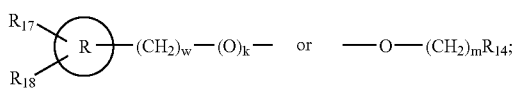

$R_{19}$ is hydrogen;

$R_{20}$ is hydrogen, lower alkyl or 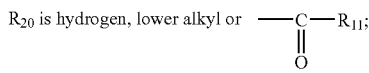

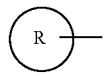

is an aryl ring, a cycloalkyl ring containing from 2 to 6 carbon atoms, a 4 to 6 membered heterocyclic alkyl ring containing from 1 to 2 hetero atoms selected from the group consisting of a oxygen, sulfur and nitrogen or a 5 to 6 numbered heteroaromatic right containing from 1 to 2 hetro atoms selected from the group consisting of oxygen sulfur and nitrogen;

$R_8$ and $R_9$ are independently hydrogen or lower alkyl;
$R_{10}$ and $R_{11}$ are lower alkyl;
$R_{14}$ is perfluoro lower alkyl;
$R_{17}$ and $R_{18}$ are independently hydrogen, lower alkyl, or

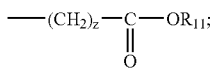

n and k are integers from 0 to 1;
w, y and z are integers from 0 to 3;
p is an integer from 0 to 6; and
v and m are integers from 1 to 6;
or N-oxides of compounds where $R_2$ contains a nitrogen in the heteroaromatic ring, sulfones where $R_2$ contains a sulfur in the heterocycloalkyl ring or heteroaromatic ring;
or pharmaceutically acceptable salts thereof that inhibit the activity of CDKs, particularly, CDK1.

These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula and compositions containing these compounds useful in treating diseases medicated by kinase activity, particularly as antitumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are the compounds of the formula:

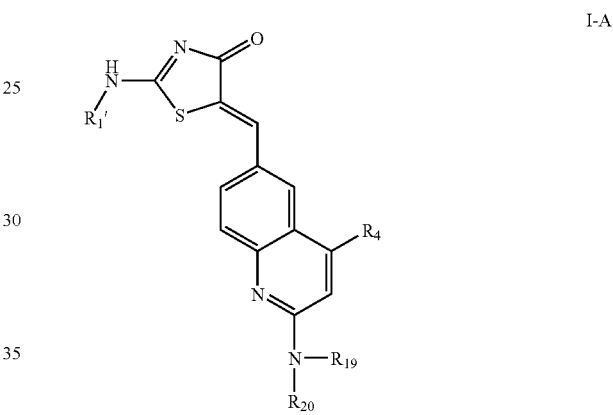

I-A wherein $R_1'$ is hydrogen, or lower alkyl, or lower alkoxy alkyl and $R_4$, $R_{19}$ and $R_{20}$ are as above; or
pharmaceutically acceptable salts thereof and compounds of the formula:

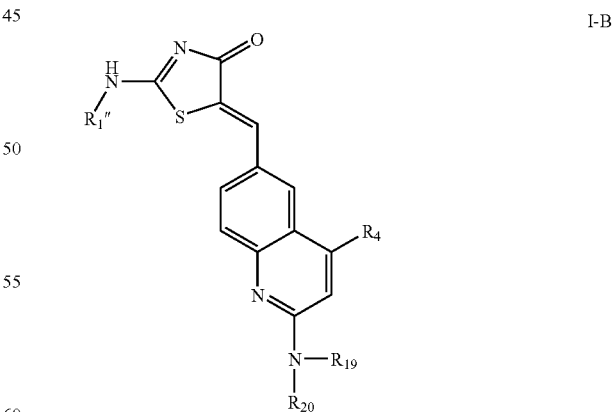

I-B wherein
$R_1''$ is $R'_2-(X')_n-$;
n, $R_4$, $R_{19}$ and $R_{20}$ are as above; and
X is lower alkylene, hydroxyloweralkylene, cyclolower alkylene, hydroxy lower alkylene, or mono- or di-halo lower alkylene;

$R_2'$ is

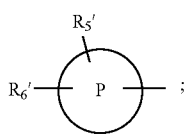

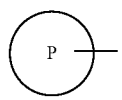

is an aryl ring, cycloalkyl ring containing from 2 to 6 carbon atoms, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen; $R_5'$ and $R_6'$ are independently selected from the group consisting of hydroxy, lower alkyl-sulfone, hydroxy-lower alkyl, hydrogen, lower alkyl, halogen, perfluro lower alkyl, lower alkoxy, amino, mono- or di-lower alkyl amino;

or N-oxides of compounds where $R'_2$ contains a nitrogen in the heteroaromatic ring, sulfones where $R_2'$ contains a sulfur in the hetero ring or heteroaromatic ring;

or pharmaceutically acceptable salts thereof.

In compounds I and I-B, where $R_1$, $R_1''$, $R_2$ and X are substituents containing an aryl moiety, the preferred aryl moiety is phenyl. As used herein, halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which designates a monovalent unsubstituted 3- to 6-membered saturated carbocylic hydrocarbon ring. Among the preferred cycloalkyl substituents are cyclopropyl, cyclobutyl, cyclohexyl, etc.

The term "lower alkoxy" means a straight-chain or branched-chain alkoxy group formed from lower alkyl containing from one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring such as phenyl or naphthyl, with phenyl being preferred.

The term "heterocycloalkyl" refers to a 4 to 6 membered monocyclic saturated ring containing 3 to 4 carbon atoms and one or two hetero atoms selected from the group consisting of oxygen, nitrogen or sulfur. Among the preferred heterocyclic alkyl groups are included mopholinyl, tetrahydro, thiopyranyl or tetrahydro pyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen or sulfur. Among the preferred heteroaromatic groups are included thiopenyl, thioazole, pyridinyl, furanyl, etc.

The term "lower alkylene" designates a divalent saturated straight or branch chain hydrocarbon substituent containing from one to six carbon atoms.

The term "carboxy lower alkylene" denotes a lower alkylene substituent as designated hereinbefore substituted, preferably monosubstituted, with a carboxy radical.

The term "hydroxy lower alkylene" designates a lower alkylene substituent substituted, preferably monosubstituted, with a hydroxy group where an amido lower alkylene is used, thus designates a lower alkylene substituent as set forth hereinbefore substituted with an amido substituent.

The term "mono- or di-halo lower alkylene substituents" designate a lower alkylene substituent which is either monosubstituted or disubstituted on one or two carbon atoms in the lower alkylene chain.

The term "amino lower alkylene" designates a lower alkylene substituent which is substituted, preferably monosubstituted, with an amino group.

The term "amido lower alkylene" designates a lower alkylene substituent as hereinbefore defined substituted on one position with an amido group. The amino group on the amino lower alkylene may be substituted by 1 or 2 lower alkyl groups. In the case of one lower alkyl group substitution, the term "mono-lower alkyl amino" is used. In the case of two lower alkyl substituents on the nitrogen atom of the amine group, the substituent is a "di-lower alkyl amino group."

The term "aryloxy" designates an aryloxy substituent where aryl is as above. The preferred aryl group is phenyl and the preferred aryloxy is phenoxy.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, etc with trifluoromethyl being especially preferred.

The term "pharmaceutically acceptable salts" refers to conventional acid-addition salts or base-addition salts that retain the biological effectiveness and properties of the compounds of formulas I, II, III, IV and V and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456–1457.

In accordance with this invention, the compounds of formula I can be prepared from a compound of the formula:

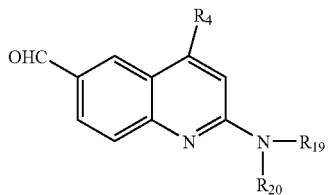

wherein $R_{19}$, $R_{20}$ and $R_4$ are as above.

The compound of formula II is converted to the compound of formula I via the following reaction scheme.

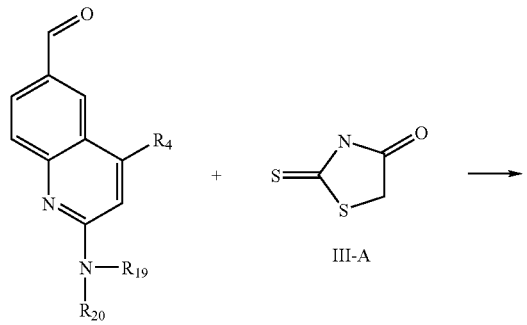

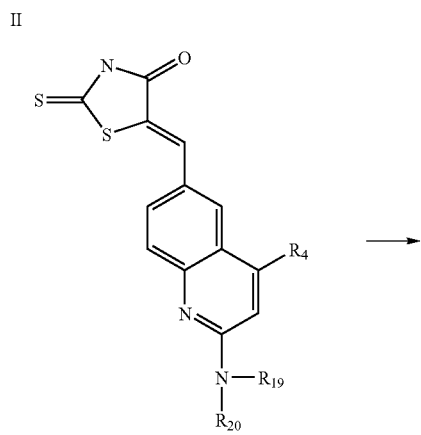

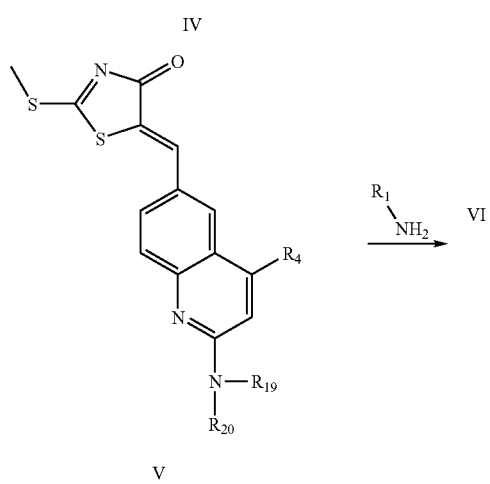

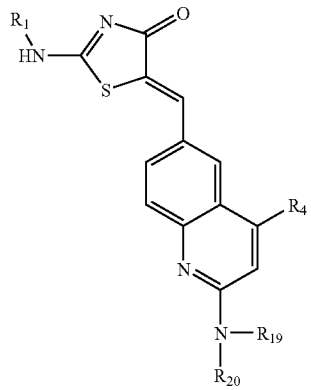

wherein
$R_1$, $R_4$, $R_{19}$ and $R_{20}$ are as above.

In accordance with this invention, the compound of formula II is reacted with the compound of formula III-A (rhodanine (2-thioxo-thiazolin-4-one)) via a Knoevenegel reaction to produce the compound of formula IV. Any of the conditions conventional in carrying out Knoevenegel reaction can be utilized in carrying out this condensation. Generally this reaction is carried out at reflux temperature in the presence of alkali metal acetate and acetic acid.

In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA). In carrying out this reaction temperature and pressure are not critical and this reaction can be carried out at room temperature and atmospheric pressure. In fact in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution of a methylthio group can be used in carrying out this reaction. In accordance with one embodiment this substitution is carried out by reacting the compound of formula VI with the compound of formula V in the presence of a conventional solvent such as acetonitrile. Generally, this reaction is carried out in the presence of an amine base such as diisopropylethylamine.

On the other hand, the compound of formula I can be prepared by reacting the compound of formula II with a compound of the formula:

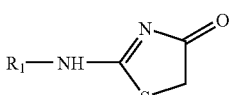

VII wherein $R_1$ is as above

The reaction of the compound of formula VII with the compound of formula II to produce the compound of formula I is carried out in a high boiling organic solvent such as benzene or toluene at high temperatures of from 150° C. to 250° C. in a closed system. In this manner this reaction is carried out under high temperatures and pressure. This reaction is specifically advantageous where it is desired to prepare compounds of formula I where the R group contains halogens in either in the chain X, or in the ring P. The compound of formula VII can be directly formed by direct replacement thorough reacting the compound of the formula $R_1$—$NH_2$     VI wherein $R_1$ is as above with a compound of the formula III-A. The replacement reaction is generally carried out in the presence of an activator for the thienyl group in the thienyl compound of formula IX and in the presence of an amine base. Among the preferred activators is mercuric chloride. This reaction is carried out in an inert organic solvent. Any conventional inert organic solvent such as acetonitrile, methylene chloride, etc. can be utilized. In carrying out this reaction, an amine base, such as diisopropylethylamine, is used. In carrying out this reaction, temperature and pressure are not critical and this reaction can be carried out at room temperature and atmospheric pressure. In carrying out this reaction, any conventional method of replacing a thienyl group with an amine can be utilized.

In the compound of formula VI where $R_1$ is X and X is a hydroxy lower alkylene, these compounds can be prepared from the corresponding amino acids or amino acid esters by reduction with an alkali metal borohydride. On the other hand, these hydroxy lower alkylene compounds can be prepared for the corresponding cyano carboxylic acid esters by reduction with lithium aluminum hydride. Reduction reduces the cyano group to an amino group and the ester to a hydroxy group. This reduction should take place before reacting the compound of formula VI with the compound of formula V.

On the other hand, where in the compound of formula VI, $R_1$ is $R_2X$— and X is a carboxy lower alkylene, amido lower alkylene or imido lower alkylene, these compounds can be directly converted to the compound of formula I by reacting the corresponding compound of formula VI with the compound of formula V or the compound of formula III-A as described above.

Where the rings Ⓟ or Ⓡ is an N-oxide of a nitrogen atom in a nitrogen containing ring which forms the rings Ⓟ or Ⓡ, these N-oxides can be formed from a tertiary ring nitrogen atom by oxidation. Any conventional method of oxidizing a tertiary nitrogen atom to an N-oxide can be utilized. The preferred oxidizing agent is metachloroperbenzoic acid (MCPBA).

The compound of formula I where R1 is hydrogen can be prepared by reacting the compound of formula II with a compound of formula VII via a Knoevenegel reaction to produce the compound of formula IV. Any of the conditions conventional in carrying out Knoevenegel reaction can be utilized in carrying out this condensation. Generally this reaction is carried out at reflux temperature in the presence of alkali metal acetate and acetic acid. In the Knoevenegel reaction of the compound of formula VII with the compound of formula II where $R_{20}$ is

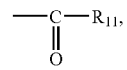

$R_{20}$ forms an amide. This amide is hydrolyzed to form an amine at the 2 position of the compound of formula I where $R_{20}$ is hydrogen. The base that is used in the Knoevenegel reaction hydrolyzes the amide group to produce the corresponding amine.

In accordance with this invention the compound of formula II where $R_4$ is hydrogen, i.e. a compound of the formula:

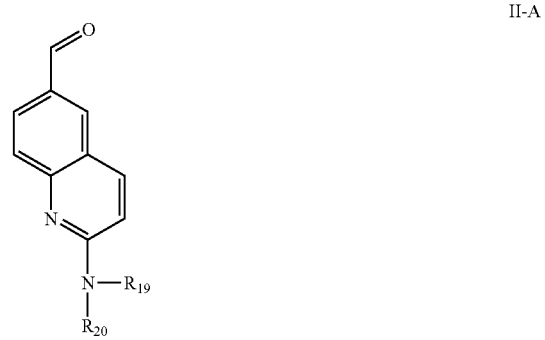

II-A where $R_{19}$ and $R_{20}$ are as above can be produced from the compound of formula

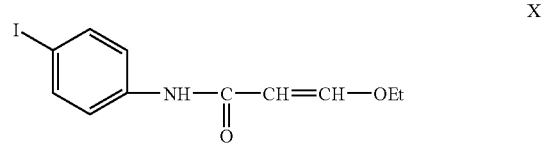

X via the following reaction scheme

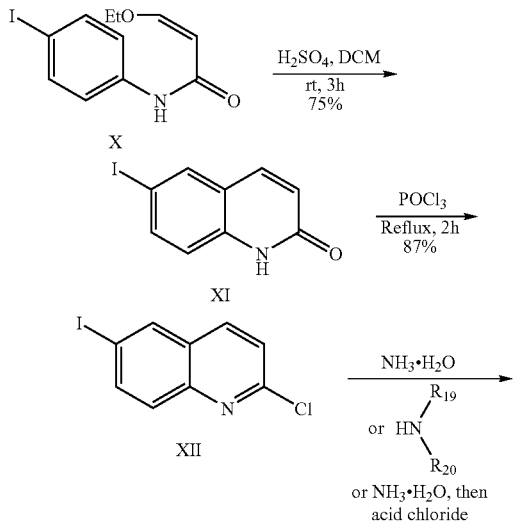

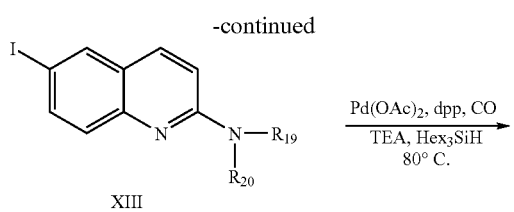

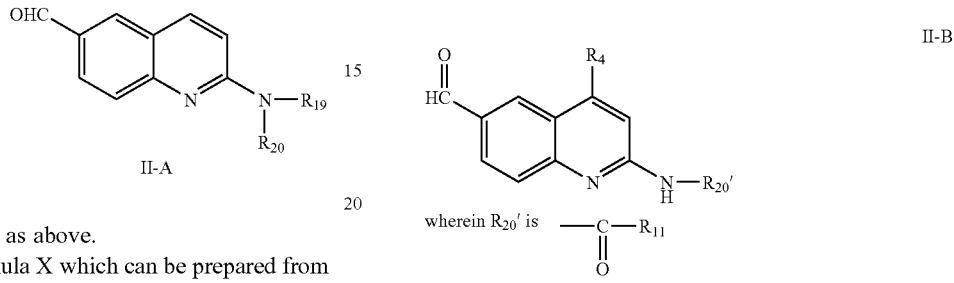

where $R_{19}$ and $R_{20}$ are as above.

The compound of formula X which can be prepared from 4-iodoaniline with 3-ethoxy-acryloyl chloride is cyclized to the compound of formula XI by treating with sulfuric acid. Generally, this reaction is carried out in an inert solvent such as dichloromethane. Cyclization is achieved through the alpha, beta unsaturated double bond in the ether moiety of the compound of formula X through the use of sulfuric acid. In carrying out this reaction, temperature and pressure are not critical and this cyclization reaction can be carried out at room temperature and atmosphere pressure. The cyclized compound of formula XI which contains the oxo substituent can be converted to the chlorinated compound of formula XII by treatment with a chlorinating agent such as phosphorous oxychloride. Generally it is preferred to use a liquid high boiling chlorinating agent such as phosphorous oxychloride. This manner the reaction mixture can be refluxed to convert the oxo substituent into the chloride with good yields. Any of the conditions conventional in converting an oxo group to a chloride group can be used in carrying out this reaction. In the next step of this reaction, the compound of formula XII is reacted with ammonium hydroxide to produce the compound of formula XIII. This reaction is carried out by reacting with ammonium hydroxide under pressure at temperatures of 100° C. to 200° C. preferably at a temperature of 150° C. for 1 to 4 hours. If desired, the secondary amine with the $R_{19}$ and $R_{20}$ substituents can be prepared by reacting the compound of formula XII with substituted amine, or by any conventional means of converting a primary amine to a secondary amine having a lower alkyl. The 2-amide substitution compound of formula II-A with

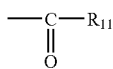

substituent thereon can be prepared by reacting the primary amine compound with the acid chloride. In the next step of this synthesis, the compound of formula XIII converted to the compound of formula II-A using formylation reaction to convert the iodo group to the CHO substituent on the phenyl ring. This reaction is carried out by reacting the compound of formula XIII with carbon monoxide in the presence of diphenyl propyl phosphine (dpp) in the presence of a base utilizing palladium acetate as catalyst. In carrying out this reaction, the carbon monoxide is added to the reaction mixture under pressure at temperature of from 60 to 100° C. Pressures generally from 70 to 80 psi are utilized in carrying out this reaction. Any conventional method of converting an halide group to the aldehyde on a phenyl ring by means of reaction with carbon monoxide can be utilized to carry out this conversion.

To produce a 2, 4 disubstituted compound of formula I, an intermediate of the formula wherein $R_4$ and $R_{11}$ is as above, one utilizes the following reaction scheme:

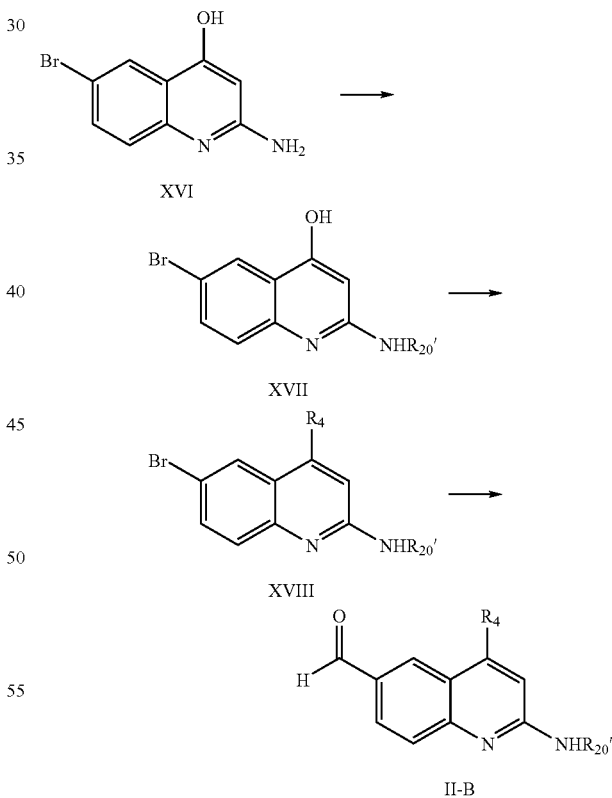

where $R_{20}'$ and $R_4$ are as above

The compound of formula XVII can be produced from the compound of formula XVI (the preparation of compound XVI was described in example 2) by reacting the compound of formula XVI with a reactive derivative of the carboxylic acid of the formula:

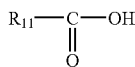

wherein $R_{11}$ is as above.

Any conventional means of converting an amine to an amide by reaction with an active carboxylic acid derivative such a halide or an anhydride can be used to carry out this reaction. The compound of formula XVII containing the hydroxy group can be converted to the compound of formula XVIII by reacting the hydroxy site of the compound of formula XVII with a halide of the $R_4$ substituent one wishes to place at the 4-position of the compound of formula 1. This reaction is carried out by reacting the corresponding halide and the compound of formula XVII under reflexing condition in an inert organic solvent medium. Any conventional method of reacting a hydroxy group with a halide can be utilized to carry out this reaction. In the last step of this synthesis, the compound of formula XVIII is converted to the compound of formula II-B using formylation reaction to convert the iodo group to the CHO substituent on the phenyl ring. This reaction can be carried out, as described heretofore by reacting the compound of formula XVIII with carbon monoxide in the presence of a base utilizing a tetrakis(triphenylphosphine)palladium catalyst at temperatures from 60° C. to 140° C. In carrying out this reaction the carbon monoxide is added to the reaction medium under pressure. Pressures from 40 to 80 psi are generally used. Any conventional method of formylation reaction to convert an halide group to the aldehyde on a phenyl ring by the means of reaction with carbon monoxide can be utilized to convert the compound of formula XVIII to the compound of formula II-B.

Among the compounds of formula I and its embodiments which include the compounds of formula I-A and formula I-B are those compounds where the aryl groups in all of the aryl substituents are preferable phenyl.

Among the preferred embodiments of the class of compounds of formula I-A are those compounds of formula I-A where $R_1$ is hydrogen. In the especially preferred embodiment of these class of compounds are those compounds where $R_4$ is $—(O)_k(CH_2CH_2O)_y—R_{10}$. In this case, compounds where $R_{20}$ is

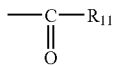

are especially preferred.

Among the preferred embodiment of the compounds of formula I-B are these class of compounds in which n is o and $R_2'$ is a cyclolower alkyl ring especially cyclopropyl. Among this class of compounds, those compounds where $R_4$ is $—(O)_k(CH_2CH_2O)_y—R_{10}$ are preferred especially preferred in this class of compounds are those compounds where $R_{20}$ is

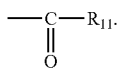

Another embodiment of this invention are those compounds of formula I-B s where n is 1 and X is lower alkylene, hydroxy lower alkylene, cyclolower alkylene or mono or dihalo lower alkylene. In this case, $R_4$ is preferably $—(O)_k(CH_2CH_2O)_y—R_{10}$. In this preferred embodiment, componds where $R_{20}$ is

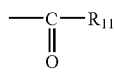

are especially preferred.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition. The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788–16801 (1998); Connell-Crowley and Harpes, Cell Cycle: Materials and Methods, (Michele Pagano, ed. Springer, Berlin, Germany)

(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

5-[1-(2-Amino-quinolin-6-yl)-meth-(Z)-ylidene]-2-((1R,2S)-2-phenyl-cyclopropylamino)-thiazol-4-one; compound with trifluoro-acetic acid

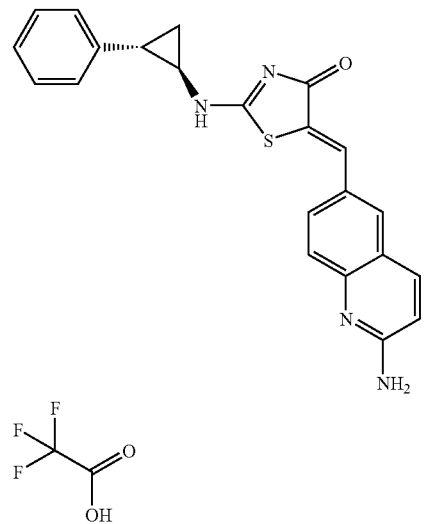

a) Preparation of 3-ethoxy-N-(4-iodo-phenyl)-acrylamide

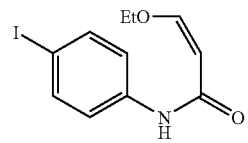

To the solution of oxalyl chloride (40 g, 0.555 mol) was slowly added ethyl vinylether (105.6 g, 0.84 mol) at 0°C. the mixture was stirred at 0°C for 2 hours and room temperature for 12 hours. After removal of some solvent by rotary evaporator, the black mixture was refluxed at 120° C. for 30 min. After removal of the solvent by rotary evaporator and then oil pump, 3-ethoxy-acryloyl chloride (69.9 g) was obtained as a black liquid which was directly used for next step reaction without further purification.

To the mixture of 4-iodoaniline (14 g, 64 mmol) and pyridine (10.5 mL, 128 mmol) in methylene chloride (85 mL) was added 3-ethoxy-acryloyl chloride (10 g, 75 mmol). After stirring for 5 hrs, more 3-ethoxy-acryloyl chloride (5 g, 38 mmol) and pyridine (10.5 mL, 64 mmol) was added. After stirring for 2 days, the reaction mixture was washed with water 3×100 mL), dried over MgSO4 and concentrated to give 3-ethoxy-N-(4-iodo-phenyl)-acrylamide as black oil (11.32 g, 56%). LC-MS m/e 318 (MH⁺).

b) Preparation of 6-iodo-1H-quinolin-2-one

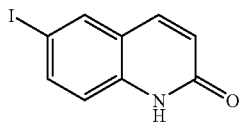

Sulfuric acid was slowly added to 3-ethoxy-N-(4-iodo-phenyl)-acrylamide (11.3 g, 36 mmol) with stirring. After stirring for 3 hrs, the reaction mixture was slowing poured into ice (~300 g). The precipitation was collected by filtration, washed with water and dried. Flash chromatography (Merck Silica gel 60, 230–400 mesh, 0%-15% methanol in methylene chloride in 40 min) afforded 6-iodo-1H-quinolin-2-one (7.23 g, 75%) as a black solid. LC-MS m/e 272 (MH⁺).

c) Preparation of 2-chloro-6-iodo-quinoline

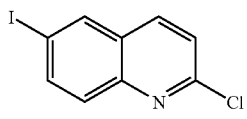

A mixture of 6-iodo-1H-quinolin-2-one (6.23 g, 23 mmol) in phosphorus oxychloride (25 mL) was refluxed under $N_2$ for 2 h. After cooling, the solvent was removed by rotary evaporator and then by the oil pump. Sat. sodium bicarbonate (100 mL) was slowly added. The solid was collected by filtration, washed with sat. sodium bicarbonate, water and dried to obtain 2-chloro-6-iodo-quinoline (5.78 g, 87%) as a black solid. LC-MS m/e 290 (MH⁺).

d) Preparation of 6-iodo-quinolin-2-ylamine

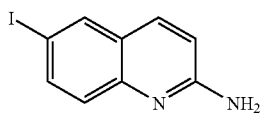

A suspension of 2-chloro-6-iodo-quinoline (1 g, 3.46 mmol) in ammonium hydroxide (28%, 20 mL) was heated at 140° C. for 3 days under pressure tube. After cooling, the solvent was removed by rotary evaporator. The solid was collected by filtration, washed with water and dried to obtain 6-iodo-quinolin-2-ylamine (0.78 g, 84%) as a black solid. LC-MS m/e 271 (MH⁺).

e) Preparation of 2-amino-quinoline-6-carbaldehyde

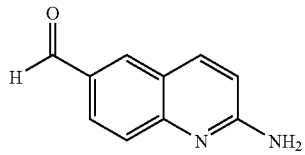

A mixture of 6-iodo-quinolin-2-ylamine (200 mg, 0.74 mmol), triethylamine (0.26 mL, 1.85 mmol), diphenylpropylphosphine (dpp, 17 uL, 0.074 mmol) and palladium(II) acetate (17 mg, 0.074 mmol) in dry N,N-dimethylformamide (4 mL) in pressure tube was stirred under carbon monoxide at 75 psi at room temperature for 10 min. After addition of trihexylsilane (0.53 mL, 1.5 mmol), the mixture was then stirred under carbon monoxide at 75 psi at 80° C. for 4 h. The reaction was allowed to cool to 25[ ]C and then extracted with methylene chloride (2×50 mL). The combined organic layers were successively washed with water (3×50 mL), dried over sodium sulfate, filtered, and concentrated in vacuo. Flash chromatography (Merck Silica gel 60, 70–230 mesh, ethyl acetate) afforded 2-amino-quinoline-6-carbaldehyde (30 mg, 24%) as a solid.

f) Preparation of 2-((1R,2S)-2-phenyl-cyclopropylamino)-thiazol-4-one

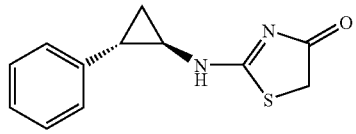

To a suspension of (1R,2S)-2-phenyl-cyclopropylamine hydrochloride (0.85 g, 5 mmol) and rhodanine (2-thioxo-thiazolin-4-one) (0.68 g, 5 mmol) in acetonitrile (20 mL) was added (N,N-diisopropylethylamine) (DIEA) (2.61 mL, 15 mmol) at room temperature. Then, this solution was cooled to 0° C. and mercuric chloride (1.35 g, 5 mmol) was added in two portions within a period of 10 min. After addition, the suspension was allowed to warm to room temperature and stirred for 2 days. The resulting black solids were filtered through a plug of celite and washed with ethyl acetate (500 mL). The filtrates were removed under the vacuum and the crude residue was diluted with water (100 mL) and ethyl acetate (100 mL). The two layers were separated and the aqueous layer was extracted with ethyl acetate (2×100 mL). The combined organic extracts were washed with brine solution and dried over anhydrous magnesium sulfate. Filtration of the drying agent and removal of the solvent under the vacuum gave the crude residue which was purified by using a Biotage silica gel column chromatography to obtain 0.474 g (42% yield) of 2-((1R,2S)-2-phenyl-cyclopropylamino)-thiazol-4-one as a white amorphous solid: EI-HRMS m/e calcd for $C_{12}H_{12}N_2OS$ (M⁺) 232.0670. found 232.0665.

g) Preparation of 5-[1-(2-amino-quinolin-6-yl)-meth-(Z)-ylidene]-2-((1R,2S)-2-phenyl-cyclopropylamino)-thiazol-4-one; compound with trifluoroacetic acid

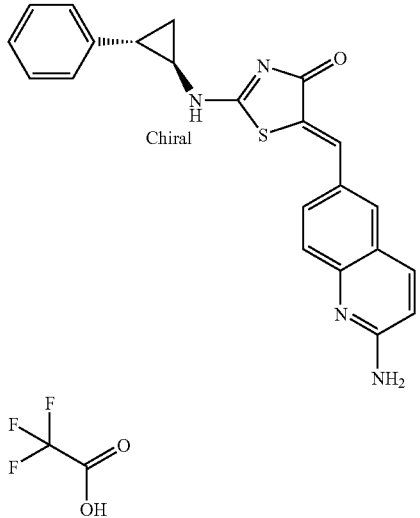

To the suspension of 2-amino-quinoline-6-carbaldehyde (30 mg, 0.174 mmol) and 2-((1R,2S)-2-phenyl-cyclopropylamino)-thiazol-4-one (26 mg, 0.11 mmol) in toluene (1 mL) was added benzolic acid (3 mg, 0.011 mmol) and piperidine (3 uL, 0.011 mmol). The mixture was heated to 150° C. by microwave for 20 min. After cooling to rt, the solid was collected by filtration, washed with toluene and dried. The crude product was purified by HPLC (Reverse C18, 10%–90% acetonitrile in water in 10 min) to afford 5-[1-(2-amino-quinolin-6-yl)-meth-(Z)-ylidene]-2-((1R,2S)-2-phenyl-cyclopropylamino)-thiazol-4-one; compound with trifluoro-acetic acid (36 mg, 84%) as a yellow solid. LC-MS m/e 271 (MH$^+$).

Example 2

5-(2-Amino-4-ethoxy-quinolin-6-ylmethylene)-2-[2-(3-fluoro-phenyl)-ethylamino]-thiazol-4-one

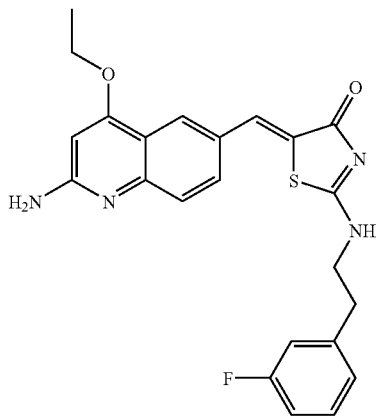

a) Preparation of 6-bromo-1H-benzo[d][1,3]oxazine-2,4-dione

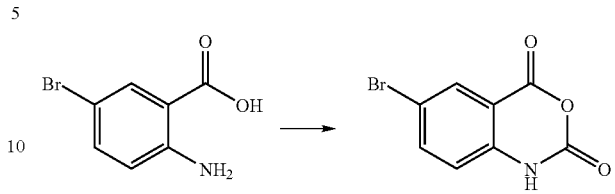

A solution of 2-amino-5-bromo-benzoic acid (280 g, 1.3 mol) in acetonitrile (1.3 l) was warmed up to 50–55° C. Pyridine (206 g, 2.61 mol) and a solution of triphosgene (128.8 g, 0.43 mol) in dichloromethane (720 ml) were simultaneously added dropwise. After completion of the addition, the mixture was stirred at 50–55° C. for an additional 2 h. The solvent was removed under reduced pressure and water was added. The precipitate was collected by filtration, successively washed with water and chilled dichloromethane, and then dried under vacuum to afford the desired product 6-bromo-1H-benzo[d][1,3]oxazine-2,4-dione (304 g, 98%). This material was used in the next step without further purification.

b) Preparation of 2-amino-6-bromo-quinolin-4-ol

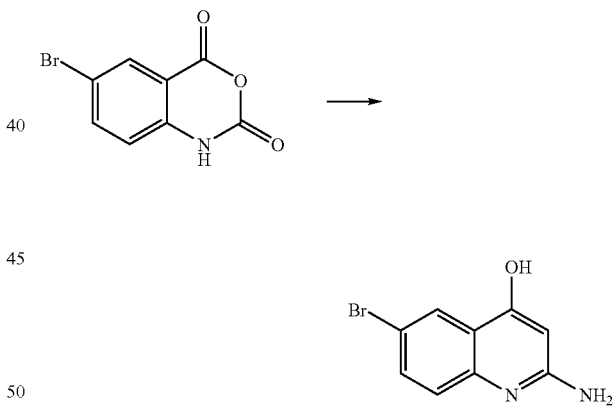

A solution of 6-bromo-1H-benzo[d][1,3]oxazine-2,4-dione (90 g, 0.373 mol) in (N,N-dimethylformamide) (DMF) (400 ml) was added to a solution of malonitrile (37 g, 0.41 mol) and triethylamine (41.4 g, 0.41 mol) in DMF (150 ml) at 50–60° C. The reaction mixture was maintained at 50–60° C. for 30 min. A reverse quench into ice-cold 0.2N HCl (400 ml) produced a precipitate. This material was isolated by filtration and vacuum dried. It was then dissolved in 8 N KOH (2 l) and the solution was refluxed for 40 h. After cooling to rt, the mixture was neutralized with HCl, and the resulting precipitate was filtered and air dried to afford 2-amino-6-bromo-quinolin-4-ol as a pale yellow solid (95 g, 97%). This material was used in the next step without further purification.

c) Preparation of N-(6-bromo-4-hydroxy-quinolin-2-yl)-acetamide

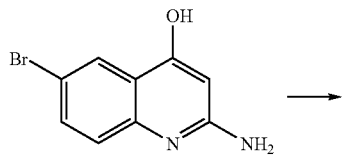

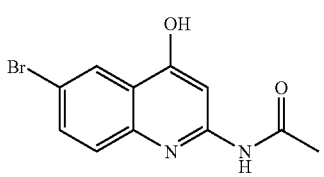

A mixture of 2-amino-6-bromo-quinolin-4-ol (29.4 g, 0.12 mol), acetic anhydride (36.7 g, 0.36 mol) and sulphuric acid (20 ml) in glacial acetic acid (300 ml) was refluxed for 30 min. The mixture was allowed to cool to rt and then poured into water. The precipitate was isolated by filtration and dried to afford product N-(6-bromo-4-hydroxy-quinolin-2-yl)-acetamide as a brown solid (32 g, 93%). This material was used in the next step without further purification.

d) Preparation of N-(6-bromo-4-ethoxy-quinolin-2-yl)-acetamide

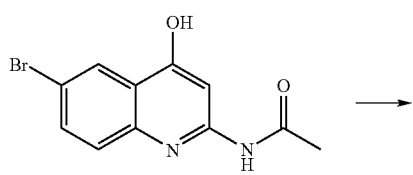

A mixture of N-(6-bromo-4-hydroxy-quinolin-2-yl)-acetamide (32 g, 0.114 mol), ethyl iodide (26.77 g, 0.171 mol) and potassium carbonate (130 g, 0.912 mol) in acetonitrile (250 ml) was refluxed for 2 h. The solvent was evaporated and the residue was triturated with water. The precipitate was collected by filtration and dried to afford N-(6-bromo-4-ethoxy-quinolin-2-yl)-acetamide as a pale yellow solid (28 g, 80%). This material was used in the next step without further purification.

e) Preparation of N-(4-ethoxy-6-formyl-quinolin-2-yl)-acetamide

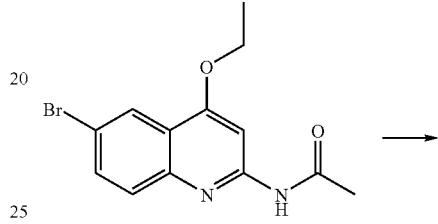

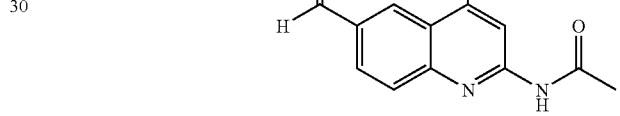

A mixture of tetrakis(triphenylphosphine)palladium (Pd(PPh$_3$)$_4$) and sodium formate (5 g, 48 mmol) in acetonitrile (30 ml) was purged with nitrogen. A solution of N-(6-bromo-4-ethoxy-quinolin-2-yl)-acetamide (2.5 g, 8.12 mmol) in DMSO (30 mL) was added through a rubber septum. The vessel was put under an atmosphere of carbon monoxide (50 psi), sealed and heated to 120° C. for 30 min. The mixture was cooled to rt and the acetonitrile was evaporated under reduced pressure. Water was added and the resulting precipitate was collected by filtration and dried to afford the desired aldehyde N-(4-ethoxy-6-formyl-quinolin-2-yl)-acetamide as a pale yellow solid (0.8 g, 40%).

f) Preparation of 5-(2-amino-4-ethoxy-quinolin-6-ylmethylene)-2-[2-(3-fluoro-phenyl)-ethylamino]-thiazol-4-one

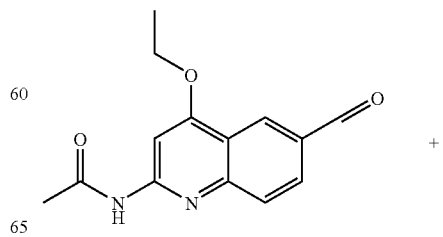

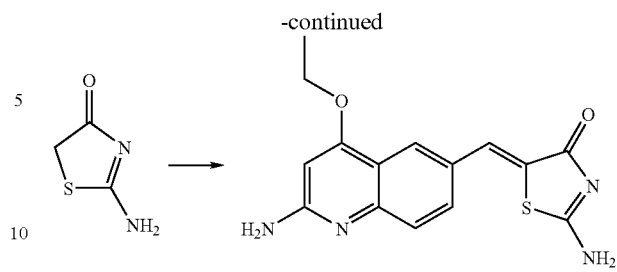

A solution of N-(4-ethoxy-6-fromyl-quinolin-2-yl)-acetamide (example 2e, 50 mg, 0.19 mmol) in acetic acid (1.5 ml) was treated with pseudothiohydantoin (34 mg, 0.29 mmol) and sodium acetate (63 mg, 0.77 mmol) in a microwave synthesizer at 180° C. for 45 min. The mixture was partitioned between 1N NaOH and dichloromethane. The aqueous layer, which contained the desired product, was concentrated to dryness and the crude residue was purified by RP HPLC to afford the product as the TFA salt (5 mg, 8%). LC-MS m/e 315 (MH+).

Example 4

N-(4-Ethoxy-6-{4-oxo-2-[(tetrahydro-pyran-4-ylmethyl-amino)-4H-thiazol-5-ylidenemethyl}-quinolin-2-yl]-acetamide

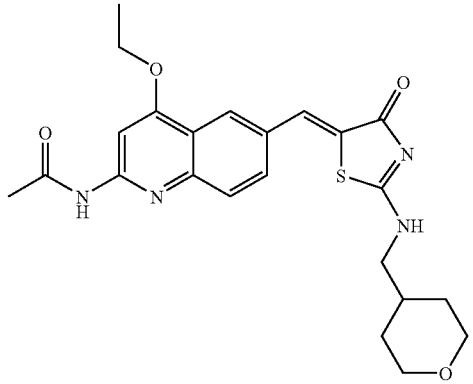

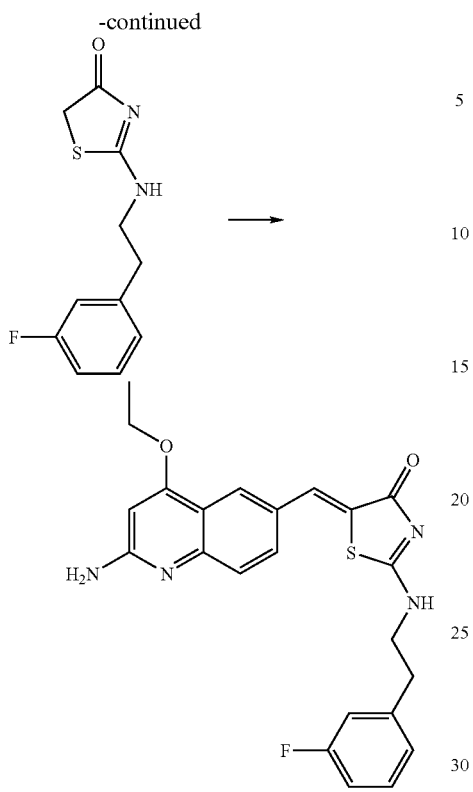

A solution of N-(4-ethoxy-6-fromyl-quinolin-2-yl)-acetamide (example 2e, 50 mg, 0.19 mmol) in acetic acid (1.5 ml) was treated with 2[2-(3-fluoro-phenyl)-ethylamino]-thiazol-4-one (69 mg, 0.29 mmol) and sodium acetate (63 mg, 0.77 mmol) in a microwave synthesizer at 180° C. for 60 min. Water (0.5 ml) was added and the reaction mixture was microwaved at 140° C. for 15 min. The mixture was quenched with 1N NaOH. The precipitate was collected by suction filtration, and successively washed with water, ether and dichloromethane. The crude precipitate was then dissolved in DMF and concentrated to dryness. This material was triturated with hot dioxane and filtered. The mother liquor was concentrated under reduced product to afford the product 5-(2-amino-4-ethoxy-quinolin-6-ylmethylene)-2-[2-(3-fluoro-phenyl)-ethylamino]-thiazol-4-one as a powder (23 mg, 28%). LC-MS m/e 437 (MH+)

Example 3

2-Amino-5-(2-amino-4-ethoxy-quinolin-6-ylmethylene)-thiazol-4-one

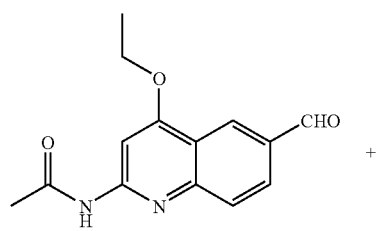

+ a) Preparation of c-(tetrahydro-pyran-4-yl)-methylammonium acetate

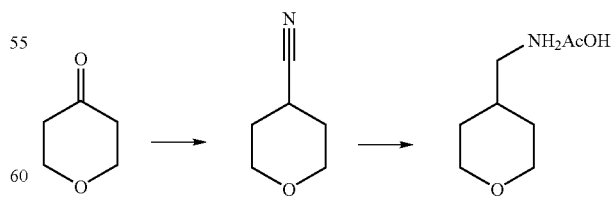

A cold (ice water bath) solution of tetrahydro-4H-pyran-4-one (7.5 g, 75 mmol) and tosylmethylisocyanide (16.05 g, 82.4 mmol) in DME (125 ml) was treated with a suspension of potassium t-butoxide (16.8 g, 150 mmoles) in t-butyl alcohol (250 ml). The reaction mixture was stirred at room temperature for 3^(1/2) hours, and then diluted with ether (250 ml). The mixture was successively washed with water and brine, then dried over sodium sulfate, filtered, and concentrated. The crude product was purified by short path distillation under high vacuum to give the nitrile as colorless oil (2.98 g). This material was dissolved in 1M borane/tetrahydrofuran (THF) (134 ml, 134 mmol) and stirred at rt overnight. Excess borane was quenched by adding methanol (rt, 1 h), and the mixture was concentrated to dryness. The residue was dissolved in 4N HCl/dioxane, stirred at rt for 1 h and then concentrated under reduced pressure. The solid residue was triturated with ether and collected by suction filtration. A suspension of this material (1.81 g, 11.9 mmol) in THF (30 ml) was treated with 1N NaOH (11.9 ml, 11.9 mmol) at rt for ½ h. The THF was removed by distillation and the aqueous solution was saturated with NaCl then extracted with dichloromethane. The organic layer was dried over sodium sulfate and concentrated under reduced pressure. The residue was treated with acetic acid (0.68 ml, 11.9 mmol) to provide, after drying in a vacuum oven, c-(tetrahydro-pyran-4-yl)-methylammonium acetate (1.71 g).

a) Preparation of N-(4-ethoxy-6-{4-oxo-2-[(tetrahydro-pyran-4-ylmethyl-amino)-4H-thiazol-5-ylidenemethyl}-quinolin-2-yl]-acetamide

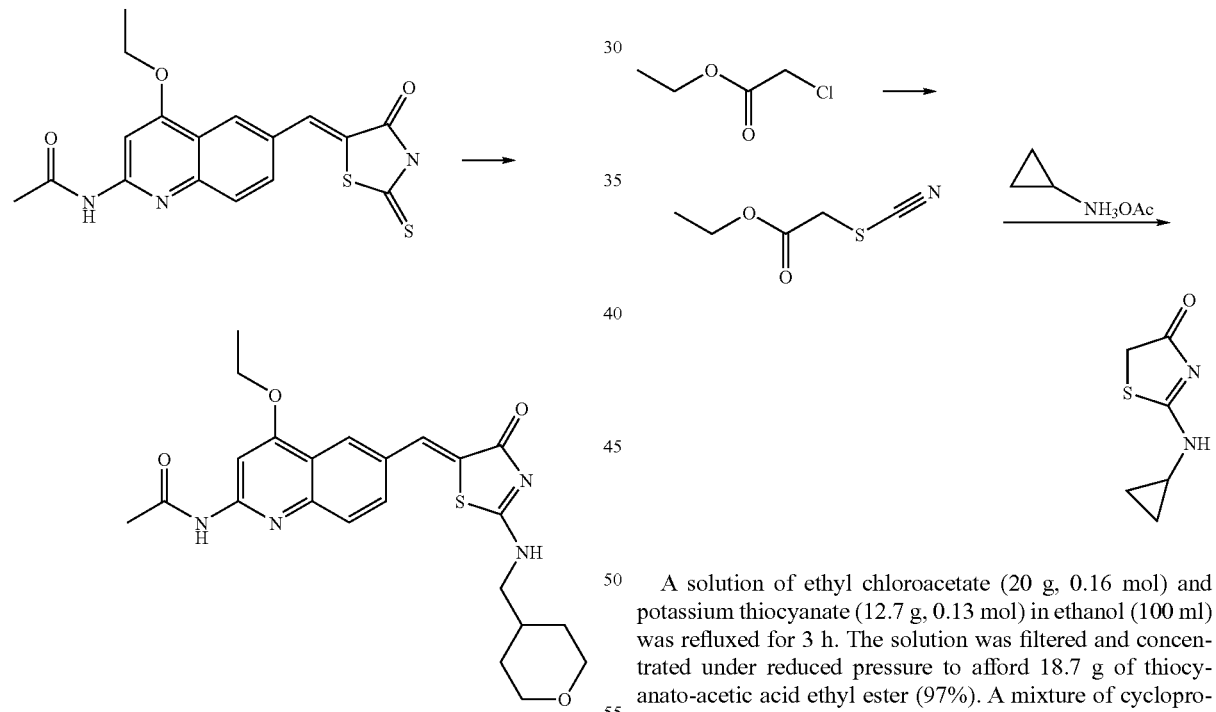

A suspension of N-[4-ethoxy-6-(4-oxo-2-thioxo-thiazolidin-5-ylidenemethyl)-quinolin-2-yl]-acetamide (example 6a, 50 mg, 0.12 mmol) in acetonitrile (2 ml) was reacted with diisopropylethyl amine (0.20 ml, 1.2 mmol) and methyl iodide (0.15 ml, 2.3 mmol) at rt for 45 min. The mixture was concentrated to dryness and the residue suspended in acetonitrile (2 ml). Diisopropylethyl amine (0.20 ml, 1.2 mmol) and c-(tetrahydro-pyran-4-yl)-methylammonium acetate (100 mg, 0.58 mmol) were successively added at rt, and the mixture was stirred at rt overnight. The precipitate was collected by suction filtration, absorbed on SiO2 and purified on a silica gel column with a 0–10% methanol/ethyl acetate gradient to afford the product as a solid (29 mg, 56%). LC-MS m/e 455 (MH+).

Example 5

N-[6-(2-Cyclopropylamino-4-oxo-4H-thiazol-5-ylidenemethyl)-4-ethoxy-quinolin-2-yl]-acetamide

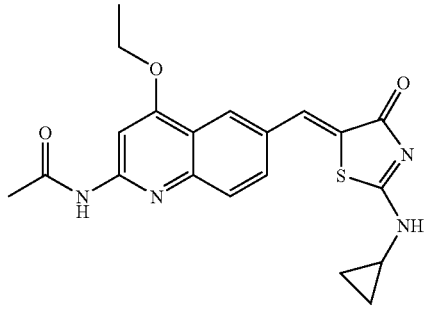

a) Preparation of 2-cyclopropylamino-thiazol-4-one

A solution of ethyl chloroacetate (20 g, 0.16 mol) and potassium thiocyanate (12.7 g, 0.13 mol) in ethanol (100 ml) was refluxed for 3 h. The solution was filtered and concentrated under reduced pressure to afford 18.7 g of thiocyanato-acetic acid ethyl ester (97%). A mixture of cyclopropylammonium acetate (0.50 g, 4.27 mmol) and thiocyanato-acetic acid ethyl ester (0.62 g, 4.27 mmol) was heated to 90° C. for 3 h, and left at rt overnight. The reaction mixture was partitioned between 6N HCl and dichloromethane. The layers were separated. The aqueous layer was made basic by the addition of 6N ammonium hydroxide, and then concentrated to dryness. The crude was triturated with dichloromethane and the solution separated from the solid by filtration. This solution was dried over sodium sulfate and concentrated to dryness. The crude was purified on a silica gel column with 100% ethyl acetate to afford 2-cyclopropylamino-thiazol-4-one (244 mg, 37%).

b) Preparation of N-[6-(2-cyclopropylamino-4-oxo-4H-thiazol-5-ylidenemethyl)4-ethoxy-quinolin-2-yl]-acetamide a) Preparation of N-[4-ethoxy-6-(4-oxo-2-thioxo-thiazolidin-5-ylidenemethyl)-quinolin-2-yl]-acetamide

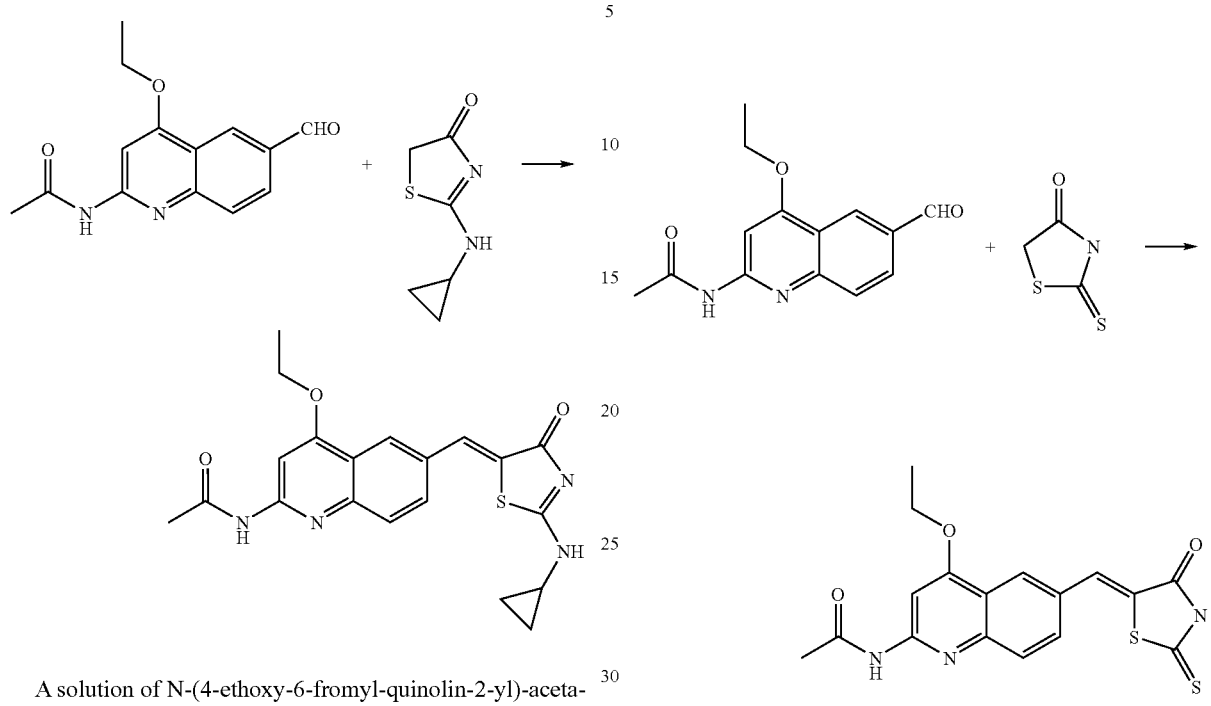

A solution of N-(4-ethoxy-6-fromyl-quinolin-2-yl)-acetamide (100 mg, 0.39 mmol) in acetic acid (2 ml) was treated with 2-cyclopropylamino-thiazol-4-one (61 mg, 0.39 mmol) and sodium acetate (127 mg, 1.55 mmol) in a microwave synthesizer at 180° C. for 90 min. The precipitate was collected by suction filtration and successively washed with water and ether to afford, after drying in a vacuum oven, the product N-[6-(2-cyclopropylamino-4-oxo-4H-thiazol-5-ylidenemethyl)-4-ethoxy-quinolin-2-yl]-acetamide as a solid (32 mg, 21%). LC-MS m/e 397 (MH$^+$).

Example 6

N-(4-Ethoxy-6-{4-oxo-2[2-(tetrahydro-pyran-4-yl)-ethylamino]-4H-thiazol-5-ylidenemethyl}-quinolin-2-yl)-acetamide A solution of N-(4-ethoxy-6-fromyl-quinolin-2-yl)-acetamide (400 mg, 1.55 mmol) in acetic acid (6 ml) was treated with rhodanine (320 mg, 0.29 mmol) and sodium acetate (530 mg, 6.5 mmol) in a microwave synthesizer at 160° C. for 25 min. The precipitate was collected by suction filtration, washed with acetic acid, water and ether, and then dried in a vacuum oven to afford intermediate N-[4-ethoxy-6-(4-oxo-2-thioxo-thiazolidin-5-ylidenemethyl)-quinolin-2-yl]-acetamide as a brown solid (396 mg, 68%).

b) Preparation of N-(4-ethoxy-6-{4-oxo-2[2-(tetrahydro-pyran-4-yl)-ethylamino]-4H-thiazol-5-ylidenemethyl}-quinolin-2-yl)-acetamide

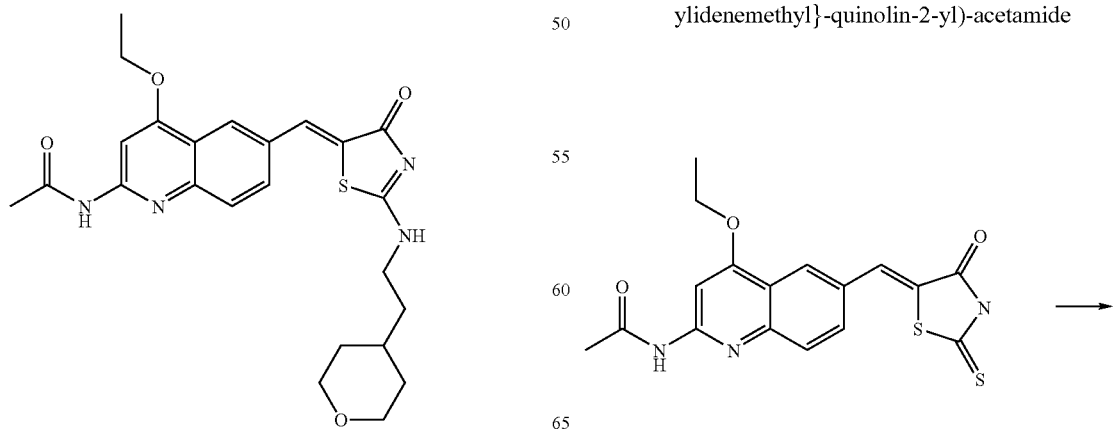

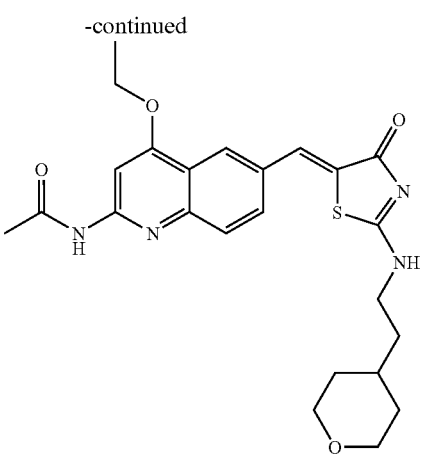

A suspension of N-[4-ethoxy-6-(4-oxo-2-thioxo-thiazolidin-5-ylidenemethyl)-quinolin-2-yl]-acetamide (example 6a, 50 mg, 0.11 mmol) in acetonitrile (1.5 ml) was reacted with diisopropylethyl amine (0.200 ml, 1.15 mmol) and methyl iodide (0.15 ml, 2.3 mmol) at rt for 30 min. The mixture was concentrated to dryness and the residue suspended in acetonitrile (1.5 ml). Diisopropylethyl amine (0.20 ml, 1.15 mmol) and 4-(2-aminoethyl)tetrahydropyran (0.075 ml, 0.58 mmol) were successively added at rt, and the mixture was stirred at rt overnight. The precipitate was collected by suction filtration, an washed with acetronitrile. It was then absorbed on SiO2 and purified on a silica gel column with a 0–10% methanol/ethyl acetate gradient to afford the product N-(4-ethoxy-6-{4-oxo-2[2-(tetrahydropyran-4-yl)-ethylamino]-4H-thiazol-5-ylidenemethyl}-quinolin-2-yl)-acetamide as a pale yellow solid (22 mg, 50%). LC-MS m/e 469 (MH$^+$).

Example 7

N-(6-{2-Amino-4-oxo-4H-thiazol-5-ylidenemethyl}-4-ethoxy-quinolin-2-yl)-acetamide

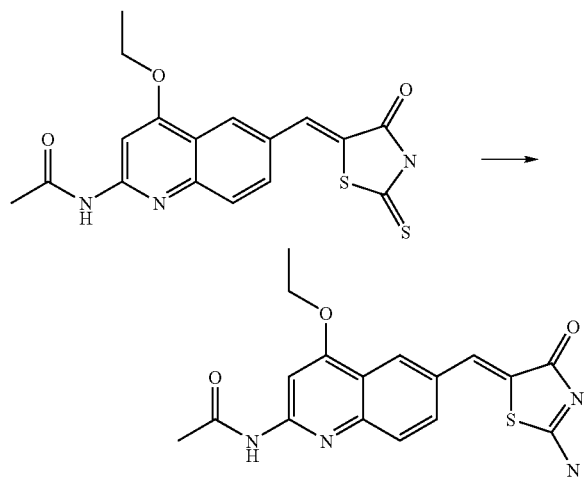

A suspension of N-[4-ethoxy-6-(4-oxo-2-thioxo-thiazolidin-5-ylidenemethyl)-quinolin-2-yl]-acetamide (example 6a, 80 mg, 0.21 mmol) in acetonitrile (3 ml) was reacted with diisopropylethyl amine (0.40 ml, 2.2 mmol) and methyl iodide (0.30 ml, 4.6 mmol) at rt for 30 min. The mixture was concentrated to dryness and the residue suspended in DMF (0.5 ml). A solution of ammonia in methanol (7N, 5 ml, 35 mmol) was added at rt, and the mixture was stirred at rt for 24 h. The mixture was concentrated to dryness and the solid was triturated with water. The precipitate was collected by suction filtration, successively washed with water and ether, and then air dried to afford the product as a light brown solid (50 mg, 663%). LC-MS m/e 357 (MH$^+$).

Example 8

N-[6-(2-Cyclopropylmethylamino-4-oxo-4H-thiazol-5-ylidenemethyl)-4-ethoxy-quinolin-2-yl]-acetamide b) Preparation of 2-cyclopropylmethylamino-thiazol-4-one

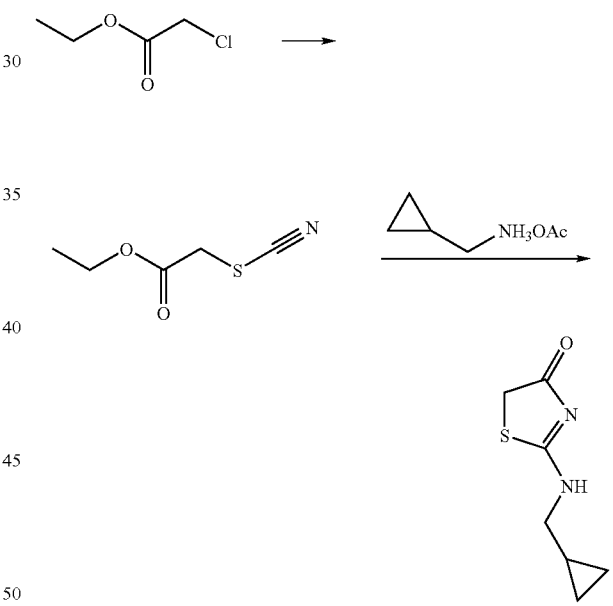

A mixture of cyclopropylmethylammonium acetate (0.45 g, 3.44 mmol) and thiocyanato-acetic acid ethyl ester (0.5 g, 3.44 mmol) was heated to 90° C. for 2 h. The reaction mixture was partitioned between 6N HCl and dichloromethane. The layers were separated. The aqueous layer was made basic by the addition of 6N ammonium hydroxide, and then extracted with dichloromethane. The organic layer was dried over sodium sulfate and concentrated under reduced pressure. The aqueous layer was also concentrated to dryness and the residue was triturated with DMF. The DMF solution was filtered and concentrated to dryness. The residues were combined and purified on a silica gel column with 100% ethyl acetate to afford 2-cyclopropylmethylamino-thiazol-4-one (275 mg, 47%).

b) Preparation of N-[6-(2-cyclopropylmethylamino-4-oxo-4H-thiazol-5-ylidenemethyl)-4-ethoxy-quinolin-2-yl]-acetamide

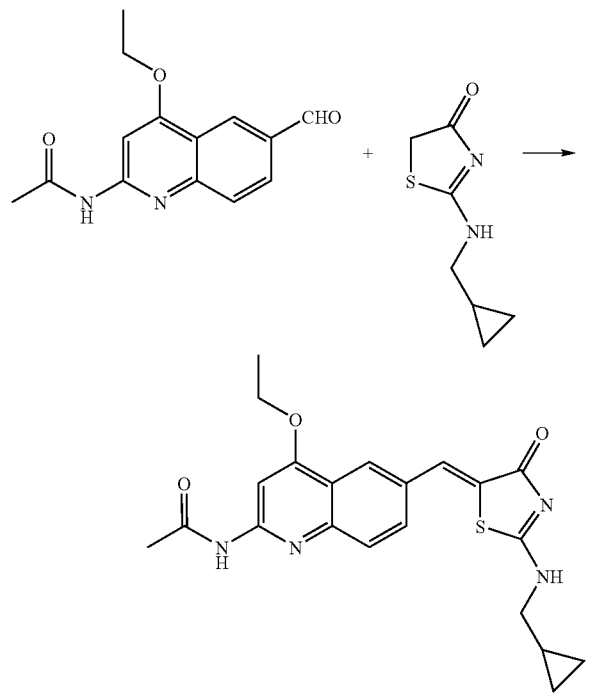

A solution of N-(4-ethoxy-6-fromyl-quinolin-2-yl)-acetamide (100 mg, 0.39 mmol) in acetic acid (2 ml) was treated with 2-cyclopropylmethylamino-thiazol-4-one (66 mg, 0.39 mmol) and sodium acetate (127 mg, 1.55 mmol) in a microwave synthesizer at 180° C. for 2 h. The reaction mixture was partitioned between 1N NaOH and ethyl acetate/dichloromethane (1:1). The organic layer was dried over sodium sulfate, filtered and concentrated to dryness. The crude was purified on a silica gel column with a 0–7% methanol/ethyl acetate gradient to afford the product N-[6-(2-cyclopropylmethylamino-4-oxo-4H-thiazol-5-ylidenemethyl)-4-ethoxy-quinolin-2-yl]-acetamide as a solid (10 mg, 7%). LC-MS m/e 411 (MH$^+$).

Example 9

N-(6-{2-[([1,4]Dioxin-2-ylmethyl)-amino]-4-oxo-4H-thiazol-5-ylidenemethyl}-4-ethoxy-quinolin-2-yl)-acetamide

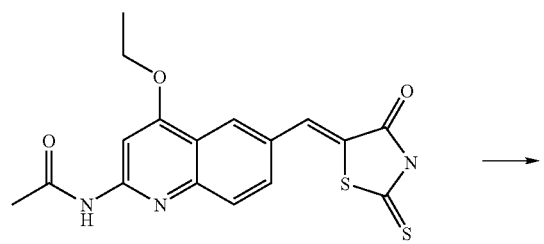

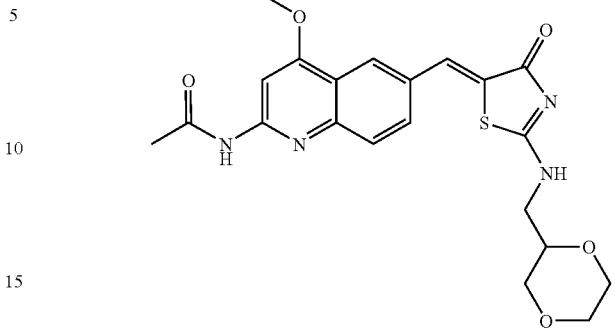

A suspension of N-[4-ethoxy-6-(4-oxo-2-thioxo-thiazolidin-5-ylidenemethyl)-quinolin-2-yl]-acetamide (example 6a, 50 mg, 0.12 mmol) in acetonitrile (1.5 ml) was reacted with diisopropylethyl amine (0.20 ml, 1.2 mmol) and methyl iodide (0.15 ml, 2.3 mmol) at rt for 30 min. The mixture was concentrated to dryness and the residue suspended in acetonitrile (1.5 ml). Diisopropylethyl amine (0.20 ml, 1.2 mmol) and c-[1,4]dioxin-2-yl-methyl amine (68 mg, 0.58 mmol) were successively added at rt, and the mixture was stirred at rt overnight. The precipitate was collected by suction filtration, absorbed on SiO2 and purified on a silica gel column with 100% ethyl acetate to afford the product N-(6-{2-[([1,4]Dioxin-2-ylmethyl)-amino]-4-oxo-4H-thiazol-5-ylidenemethyl}-4-ethoxy-quinolin-2-yl)-acetamide as a solid (34 mg, 63%). LC-MS m/e 457 (MH$^+$).

Example 10

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 µM. This demonstrates that all of these compounds were active to inhibit CDK1/Cyclin B.

Kinase Assays

To determine inhibition of CDK1 activity, either Flash-Plate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805–816). A 6x-Histidine tagged truncated form of retinoblastoma (Rb) protein (amino acid 386–928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581–601 and the references cited therein). The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM MgCl$_2$, 0.002% Tween 20, 2 mM DTT, 1 [M ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The IC$_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM MgCl$_2$, 1.5 mM DTT, and 162 µM ATP) with DMSO concentration at 15%. The CDK1/Cyclin B enzyme was diluted in kinase assay buffer 2 (25 mM HEPES, pH 7.0, 8 mM MgCl$_2$, 0.003% Tween 20, 0.045% BSA, 1.5 mM DTT, and 0.338 µM Rb protein). To initiate the kinase reaction, 20 µL of compound solution was mixed with 40 µL of CDK1/Cyclin B solution in assay plates with final concentration of CDK1/Cyclin B and Rb at 0.1 µg/mL and 0.113 µM, respectively, and incubated at 37° C. for 30 min. 15 µL of anti-phospho-Rb (Ser 780) antibody (Cell Signaling Technology, Beverly, Mass.,) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject matter of this invention ranges from about 0.001 µM to about 5.000 µM. Specific data for some examples are as follows:

| Example | Ki (µM) |
|---------|---------|
| 1       | 0.023   |
| 3       | 0.030   |
| 5       | 0.085   |
| 7       | 0.097   |
| 9       | 3.241   |

The invention claimed is:

1. A compound of the formula:

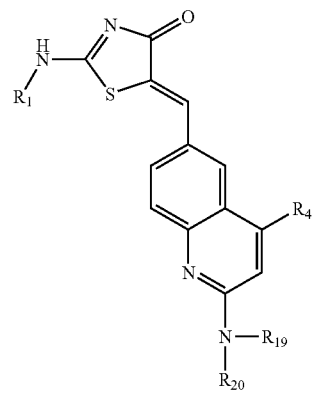

wherein

R$_1$ is hydrogen, lower alkyl, aryloxy-lower alkyl, $$-\underset{\underset{O}{\|}}{C}-O[CH_2CH_2O]_p-R_9 \text{ or } -[CH_2CH_2O]_vR_8; \text{ or } R_2-(X)n-\ ;$$

X is lower alkylene, hydroxyloweralkylene, cycloloweralkylene, aryl lower alkylene, carboxyloweralkylene, hydroxy lower alkylene, amido lower alkylene, mono- or di-halo lower alkylene, amino lower alkylene, mono- or di-lower alkyl amino lower alkylene or imido lower alkylene;

R$_2$ is 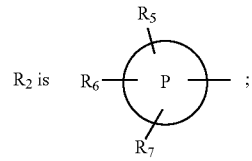 ;

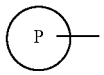

is an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, or a 5 or 6 membered heteroaromatic ring containing from 1 to 2 hetero atoms selected from the group consisting of oxygen, sulfur and nitrogen;

$R_5$, $R_6$ and $R_7$ are independently selected from the group consisting of hydroxy, lower alkyl-sulfone, hydroxy-lower alkyl, hydrogen, lower alkyl, halogen, perfluro lower alkyl, lower alkoxy, amino, mono- or di- lower alkyl amino, or when two of the substituents $R_5$, $R_6$ and $R_7$ are substituted on adjacent carbon atoms on ring (P), these two substituents can be taken together with their adjacent, attached carbon atoms to form an aryl ring, a 3 to 6 membered cyclolower alkyl ring, a 4 to 6 membered heterocycloalkyl ring or a 4 to 6 membered heteroaromatic ring, said heterocycloalkyl ring and said heteroaromatic ring containing from 1 to 2 hetero atoms selected from the group consisting of oxygen, nitrogen or sulfur;

$R_4$ is hydrogen, $-(O)_k(CH_2CH_2O)_y-R_{10}$,

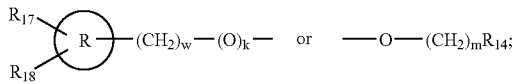

$R_{19}$ is hydrogen;
$R_{20}$ is hydrogen, lower alkyl or

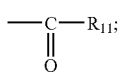

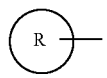

is an aryl ring, a cycloalkyl ring containing from 2 to 6 carbon atoms, a 4 to 6 membered heterocyclic alkyl ring containing from 1 to 2 hetero atoms selected from the group consisting of a oxygen, sulfur and nitrogen or a 5 to 6 numbered heteroaromatic right containing from 1 to 2 hetro atoms selected from the group consisting of oxygen sulfur and nitrogen;

$R_8$ and $R_9$ are independently hydrogen or lower alkyl;
$R_{10}$ and $R_{11}$ are lower alkyl;
$R_{14}$ is perfluro lower alkyl;
$R_{17}$ and $R_{18}$ are independently hydrogen, lower alkyl, or

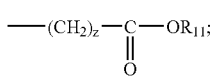

n and k are integers from 0 to 1;
w, y and z are integers from 0 to 3;
p is an integer from 0 to 6; and
v and m are integers from 1 to 6;
or N-oxides of compounds where $R_2$ contains a nitrogen in the heteroaromatic ring, sulfones where $R_2$ contains a sulfur in the heterocycloalkyl ring or heteroaromatic ring;
or pharmaceutically acceptable salts thereof.

2. The compound of claim 1 wherein said compound is:

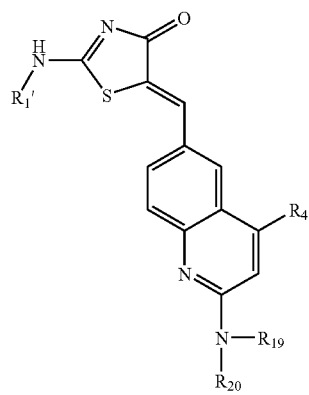

I-A wherein $R_1'$ is hydrogen, or lower alkyl; and
$R_4$, $R_{19}$ and $R_{20}$ are as above;
or pharmaceutically acceptable salts thereof.

3. The compound of claim 2 wherein $R_1'$ is hydrogen.

4. The compound of claim 3 wherein $R_4$ is $-(O)_k(CH_2CH_2O)_y-R_{10}$; and
$R_{10}$, k and y are as above.

5. The compound of claim 4 wherein said compound is N-(6-{2-amino-4-oxo-4H-thiazol-5-ylidenemethyl}-4-ethoxy-quinolin-2-yl)-acetamide.

6. The compound of claim 4 wherein said compound is 2-amino-5-(2-amino-4-ethoxy-quinolin-6-ylmethylene)-thiazol-4-one.

7. The compound of claim 1 wherein said compound is:

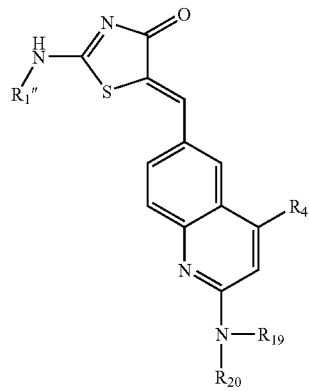

I-B wherein
$R_1''$ is $R'_2-(X')_n-$;
n, $R_4$, $R_{19}$ and $R_{20}$ are as above; and
X' is lower alkylene, hydroxyloweralkylene, cyclolower alkylene, hydroxy lower alkylene, mono- or di-halo lower alkylene;

$R_2'$ is

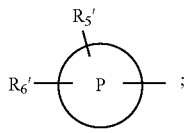

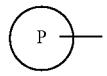

is an aryl ring, cycloalkyl ring containing from 2 to 6 carbon atoms, a 4 to 6 membered heterocycloalkyl ring containing from 3 to 5 carbon atoms and from 1 to 2 hetero atoms selected from the group consisting of oxygen, nitrogen and sulfur, a 5 or 6 membered heteroaromatic ring containing from 1 to 2 hetero atoms selected from the group consisting of oxygen, sulfur and nitrogen;

$R_5'$ and $R_6'$ are independently selected from the group consisting of hydroxy, lower alkyl-sulfone, hydroxy-lower alkyl, hydrogen, lower alkyl, halogen, perfluoro lower alkyl, lower alkoxy, amino, and mono- and di-lower alkyl amino;

or N-oxides of compounds where $R'_2$ contains a nitrogen in the heteroaromatic ring, sulfones where $R'_2$ contains a sulfur in the heterocycloalkyl ring or heteroaromatic ring;

or pharmaceutically acceptable salts thereof.

8. The compound of claim 7 wherein n is 1.
9. The compound of claim 8 wherein X' is lower alkylene.
10. The compound of claim 9 wherein the ring

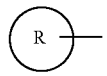

is a phenyl ring.

11. The compound of claim 10 wherein $R_4$ is $-(O)_k(CH_2CH_2O)_y-R_{10}$ and $R_{10}$, k and y are as above.

12. The compound of claim 11 wherein said compound is 5-(2-amino-4-ethoxy-quinolin-6-ylmethylene)-2-[2-(3-fluoro-phenyl)-ethylamino]-thiazol-4-one.

13. The compound of claim 9 where the ring

is a heteroalkyl ring.

14. The compound of claim 13 wherein $R_4$ is $-(O)_k(CH_2CH_2O)_y-R_{10}$ and y, k, and $R_{10}$ are as above.

15. The compound of claim 14 wherein said compound is N-(4-ethoxy-6-{4-oxo-2[2-(tetrahydro-pyran-4-yl)-ethylamino]-4H-thiazol-5-ylidenemethyl}-quinolin-2-yl)-acetamide.

16. The compound of claim 14 wherein said compound is N-(4-ethoxy-6-{4-oxo-2-[(tetrahydro-pyran-4-ylmethyl-amino)-4H-thiazol-5-ylidenemethyl}-quinolin-2-yl]-acetamide.

17. The compound of claim 14 wherein said compound is N-(6-{2-[([1,4]dioxin-2-ylmethyl)-amino]-4-oxo-4H-thiazol-5-ylidenemethyl}-4-ethoxy-quinolin-2-yl)-acetamide.

18. The compound of claim 9 wherein $R_1"$ is cycloalkyl.

19. The compound of claim 18 wherein $R_4$ is $-(O)_k(CH_2CH_2O)_y-R_{10}$ and $R_{10}$, k and y are as above.

20. The compound of claim 19 wherein said compound is N-[6-(2-cyclopropylmethylamino-4-oxo-4H-thiazol-5-ylidenemethyl)-4-ethoxy-quinolin-2-yl]-acetamide.

21. The compound of claim 7 wherein n is 0.

22. The compound of claim 21 where the ring

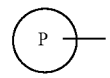

is a cycloalkyl ring.

23. The compound of claim 22 wherein $R_4$ is $-(O)_k(CH_2CH_2O)_y-R_{10}$ and $R_{10}$, k and y are as above.

24. The compound of claim 23 wherein said compound is N-[6-(2-cyclopropylamino-4-oxo-4H-thiazol-5-ylidenemethyl)-4-ethoxy-quinolin-2-yl]-acetamide.

* * * * *